United States Patent [19]

Barone et al.

[11] Patent Number: 5,360,443
[45] Date of Patent: Nov. 1, 1994

[54] AORTIC GRAFT FOR REPAIRING AN ABDOMINAL AORTIC ANEURYSM

[76] Inventors: Hector D. Barone, Maza 1869/73, Buenos Aires, Argentina, 1240; Julio C. Palmaz, 636 Ivy La., San Antonio, Tex. 78209; Juan C. Parodi, Mercedes 4255, Buenos Aires, Argentina, 1419

[21] Appl. No.: 535,745

[22] Filed: Jun. 11, 1990

[51] Int. Cl.$^5$ .................. A61F 2/06; A61M 29/02
[52] U.S. Cl. ........................... 623/1; 623/12; 606/194; 606/195
[58] Field of Search ............... 623/1, 11, 12; 606/191–200; 600/36

[56] References Cited

U.S. PATENT DOCUMENTS

| | | | |
|---|---|---|---|
| 3,657,744 | 4/1972 | Ersek | 623/1 |
| 4,140,126 | 2/1979 | Choudhury | 128/325 |
| 4,512,338 | 4/1985 | Balko et al. | 128/1 |
| 4,562,596 | 1/1986 | Kornberg | 623/1 |
| 4,577,631 | 3/1986 | Kreamer | 128/334 R |
| 4,617,932 | 10/1986 | Kornberg | 128/334 |
| 4,681,110 | 7/1987 | Wiktor | 128/343 |
| 4,739,762 | 4/1988 | Palmaz | 623/1 |
| 4,773,665 | 3/1988 | Palmaz | 128/343 |
| 4,776,337 | 10/1988 | Palmaz | 128/343 |
| 4,787,899 | 11/1988 | Lazarus | 623/1 |
| 4,902,289 | 2/1990 | Yannas | 623/1 |
| 4,922,905 | 5/1990 | Strecker | 606/195 |
| 5,078,726 | 1/1992 | Kreamer | 606/194 |

FOREIGN PATENT DOCUMENTS 2135585A 9/1984 United Kingdom .
WO9015582 12/1990 WIPO .

OTHER PUBLICATIONS

Self Expanding Endovascular Graft: An Experimental Study in Dogs; Yoshioka et al.; AJR:151 pp. 673–676 (1988).
"A Balloon–Expandable Intravascular Stent for Obliterating Experimental Aortic Dissection"; Trent et al, Presented at the Forty–Third Annual Meeting of the Society for Vascular Surgery Jun. 20, 1989.
Transfemoral Placement of Intraluminal Polyurethane Prosthesis for Abdominal Aortic Aneurysm; Balko et al, Journal of Surgical Research 40, p. 305–309 (1986.
The Surgical Experience and a One to Sixteen Year Follow-Up of 277 Abdominal Aortic Aneurysm.
Gardner et al, American Journal of Surgery 135, pp. 226–230 (1978).

*Primary Examiner*—Randall L. Green
*Assistant Examiner*—Debra S. Brittingham
*Attorney, Agent, or Firm*—Ben D. Tobor

[57] ABSTRACT

An aortic graft, and method and apparatus for repairing an abdominal aortic aneurysm includes a tubular graft which is intraluminally delivered through the aorta and secured to the aorta by the expansion and deformation of a thin-walled tubular member.

18 Claims, 4 Drawing Sheets

AORTIC GRAFT FOR REPAIRING AN ABDOMINAL AORTIC ANEURYSM

1. Field of the Invention

The invention relates to an aortic graft for intraluminal delivery, and a method and apparatus for repairing an abdominal aortic aneurysm.

2. Description of the Prior Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the arterioscleroticaly diseased aorta, for example, below the kidneys. When left untreated, the aneurysm will eventually cause rupture of the sac with ensuing fatal hemorrhaging in a very short time. High mortality associated with the rupture has led to the present state of the art and the transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of either DACRON ®, TEFLON ®, or other suitable material.

To perform the surgical procedure, requires exposure of the aorta through an abdominal incision, which can extend from the rib cage to the pubis. The aorta must be closed both above and below the aneurysm, so that the aneurysm can then be opened and the thrombus, or blood clot, and arterioscleriotic debris removed. Small arterial branches from the back wall of the aorta are tied off. The DACRON ® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aorta aneurysm, the survival rate of treated patients is markedly higher than if the surgery is performed after the aneurysm ruptures, although the mortality rate is still quite high. If the surgery is performed prior to the aneurysm rupturing, the mortality rate is typically less than 5%. Conventional surgery performed after the rupture of the aneurysm is significantly higher, one study reporting a mortality rate of 66.7%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate, are: the extended recovery period associated with such surgery; difficulties in suturing the graft, or tube, to the aorta; the loss of the existing thrombosis to support and reinforce the graft; the unsuitability of the surgery for many patients having abdominal aortic aneurysms; and the problems associated with performing the surgery on an emergency basis after the aneurysm has ruptured. As to the extent of recovery, a patient can expect to spend from 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is many times difficult to perform the suturing step because of thrombosis present on the remaining portion of the aorta, and that remaining portion of the aorta wall may many times be friable, or easily crumbled.

Since the thrombosis is totally removed in the prior art surgery, the new graft does not have the benefit of the previously existing thrombosis therein, which could be utilized to support and reinforce the graft, were the graft to be able to be inserted within the existing thrombosis. Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such surgery, which is considered major surgery. Such patients have difficulties in surviving the operation. Lastly, once the aneurysm has ruptured, it is difficult to perform a conventional surgery on an expedited basis because of the extent of the surgery.

Accordingly, prior to the development of the present invention, there has been no graft for intraluminal delivery, or method and apparatus for repairing an abdominal aortic aneurysm, which: does not have a relatively high morbidity and mortality rate; does not have an extended recovery period; does not require suturing the graft to the remaining aorta wall; permits the existing thrombosis therein to support and reinforce the graft: is suitable for older patients with chronic illnesses; and is more readily performed on an emergency basis after rupture of the aneurysm. Therefore, the art has sought an aortic graft intraluminal delivery, and method and apparatus for repairing an abdominal aortic aneurysm which is believed to: not have a high morbidity and mortality rate; does not require an abdominal incision and general anesthesia; not require an extended recovery period; not require suturing the graft to the remaining aortic wall; permit the existing aortic wall and thrombosis therein to be retained to reinforce and support the aortic graft; be suitable for patients having other chronic illnesses; and be more readily, quickly performed on an emergency basis after rupture of the aneurysm.

SUMMARY OF THE INVENTION

In accordance with the invention, the foregoing advantages have been achieved through the present aortic graft for intraluminal delivery to repair an abdominal aortic aneurysm in an aorta having two iliac arteries associated therewith. The present invention includes a tube having first and second ends and a wall surface disposed between the two ends, at least a portion of the tube adapted to be disposed within the abdominal aortic aneurysm; means for securing the first end of the tube to the aorta, the securing means including a thin-walled tubular member having first and second ends and a smooth outer wall surface disposed between the first and second ends, the wall surface having a substantially uniform thickness and a plurality of slots formed therein, the slots being disposed substantially parallel to the longitudinal axis of the tubular member; the first end of tube being secured to the second end of the tubular member; the tubular member having a first diameter which permits intraluminal delivery of the tubular member into the aorta and the tubular member having a second, expanded and deformed diameter, upon the application from the interior of the tubular member of a radially, outwardly extending force, which second diameter is variable and dependent upon the amount of force applied to the tubular member, whereby the tubular member may be expanded and deformed to secure the first end of the tubular member to the aorta.

A further feature of the present invention is that the second end of the tube may be bifurcated and two tubular passageways are formed which are in fluid communication with the first end of the tube and the two passageways are adapted to be mated with and disposed within the two iliac arteries. Another feature of the present invention is that the two tubular passageways may include means for securing the two tubular passageways to the two iliac arteries, and the securing means may be a thin-walled tubular member which has a first diameter which permits intraluminal delivery of the tubular member into the aorta, the tubular member having a second, expanded and deformed diameter, upon the application from the interior of the tubular member of a radially, outwardly extending force, which second diameter is variable and dependent upon the amount of force applied to the tubular member, whereby the tubular member may be expanded and deformed to secure the tubular member to the iliac artery. A further feature of the present invention is that the first end of the tube which may be secured to the second end of the tubular member is radially expandable, whereby the first end of the tube may conform with the second expanded and deformed diameter of the second end of the tubular member. An additional feature of the present invention is that the tube may have an intermediate portion which is not substantially radially expandable. Another feature of the present invention is that the tube may be bio-erodable, and it may be impervious to the flow of fluid through the wall surface of the tube.

In accordance with the invention, the foregoing advantages have also been achieved through the present apparatus for repairing an abdominal aortic aneurysm. The apparatus of the present invention includes: a tube having first and second ends and a wall surface disposed between the two ends; an expandable and deformable, thin-walled tubular member having first and second ends and a smooth outer wall surface disposed between the first and second ends, the first end of the tube being secured to the second of the tubular member, and the expansion and deformation of the thin-walled tubular member being controllable; and a catheter having an expandable, inflatable portion associated therewith, the thin-walled tubular member being releasably mounted upon the inflatable portion of the catheter, whereby upon inflation of the expandable, inflatable portion of the catheter, the thin-walled tubular member is forced radially outwardly into contact with the aorta to remain secured thereto, whereby the tube, secured to the thin-walled tubular member, provides a passageway through the abdominal aortic aneurysm.

In accordance with the invention, the foregoing advantages have also been achieved through the present method for repairing an abdominal aortic aneurysm in an aorta having two iliac arteries. The method of the present invention comprises the steps of: connecting a tube to an expandable and deformable, tubular member; disposing the tube and tubular member upon a catheter having an expandable, inflatable portion with the tubular member disposed upon the expandable, inflatable portion; intraluminally delivering the tube, tubular member and catheter to the aorta and disposing at least a portion of the tube within the abdominal aortic aneurysm; expanding the expandable, inflatable portion of the catheter to expand and deform the tubular member to force the tubular member radially outwardly into contact with the aorta to secure the tubular member and at least a portion of the tube within the aorta, whereby the tube provides a fluid passageway through the abdominal aortic aneurysm.

Another feature of the present invention is that the tube may have first and second ends, the first end of the tube being connected to the tubular member and the second end of the tube being bifurcated to form two tubular passageways, and the passageway is disposed in each iliac artery. A further feature of the present invention includes the steps of: connecting an expandable and deformable tubular member to each of the tubular passageways; disposing each tubular member within an iliac artery; expanding and deforming each tubular member with a catheter to secure each tubular member and associated fluid passageway within an iliac artery.

An additional feature of the present invention includes the steps of providing a biologically inert coating on the tube. A further feature of the present invention is utilizing a tube made of a material which is impervious to the flow of fluid or utilizing a tube made of a material which is bio-erodable. Another feature of the present invention is that the tube, tubular member, and catheter may be intraluminally delivered through a femoral artery. Another feature of the present invention is that the tube, tubular member, and catheter may be intraluminally delivered through an axillary artery.

The aortic graft for intraluminal delivery, and method and apparatus for repairing an abdominal aortic aneurysm of the present invention, when compared to previously proposed prior art grafts and methods and apparatus for repairing aneurysms, are believed to have the advantages of: a lower mortality rate; shortened recovery periods; not requiring suturing a graft to the aorta; utilizing the existing aortic wall and thrombosis therein to support and reinforce the aortic graft; being suitable for use with patients having other chronic illnesses; and is able to be expeditiously used on an emergency basis after an aneurysm has ruptured.

Figure 1:
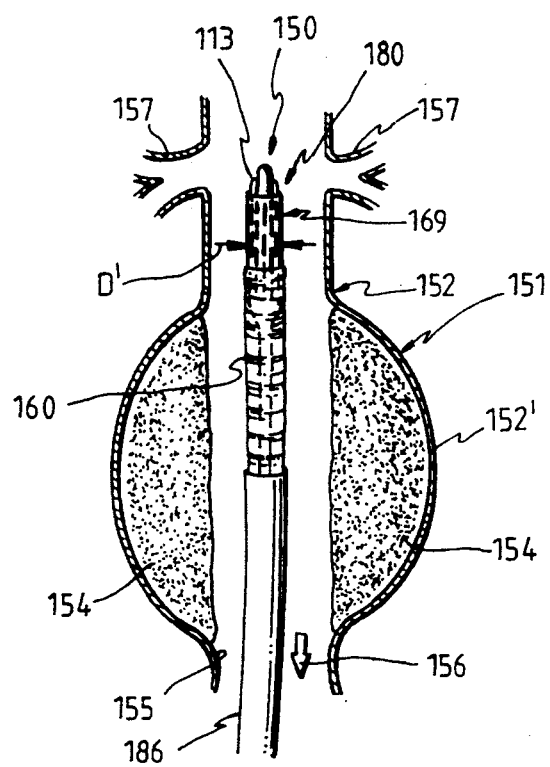
FIG. 1 is a partial cross-sectional view of an abdominal aortic aneurysm in the process of being repaired in accordance with the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims,

DETAILED DESCRIPTION OF THE INVENTION

In FIGS. 1–4 an aortic graft 150 for intraluminal delivery to repair an abdominal aortic aneurysm 151 in an aorta 152 having two iliac arteries 153L, 153R associated therewith is illustrated. Aortic graft 150, as well as other grafts to be hereinafter described, could also be utilized in the thoracic aorta, and can be used to repair thoracic aneurysms or thoracic disecting aneurysms. Accordingly, use of the term "aortic aneurysm" in this specification and claims is intended to relate to and mean both abdominal aortic aneurysms and thoracic aneurysms. Aneurysm 151 include areas of thrombosis 154, which are disposed against the interior wall surface 155 of aorta 152. Blood flows through the aorta in the direction of arrows 156. Associated with aorta 152, above aneurysm 151, are a plurality of renal arteries 157, in fluid communication with aorta 152. Aortic graft 150 is seen to generally comprise: a tube 160 having first and second ends 161. 162 and wall surface 163 disposed between the two ends, at least a portion of the tube 160 adapted to be disposed within the aneurysm 151: and means for securing 165 the first end 161 of the tube 160 to the aorta 152.

Figure 2:
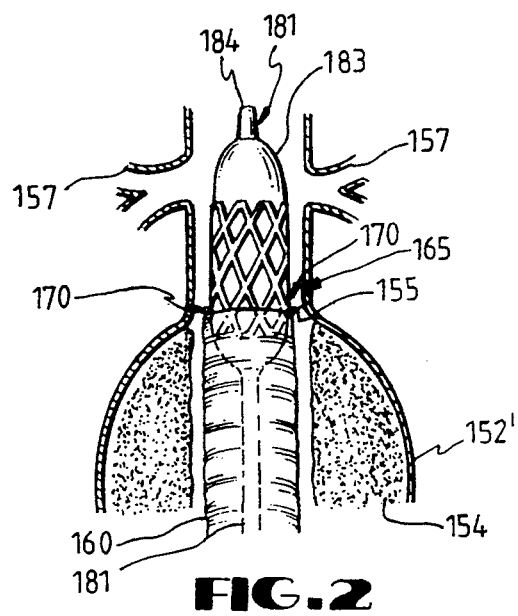
FIG. 2 is a partial cross-sectional view of a portion of the aorta of FIG. 1, illustrating the expansion of a portion of an aortic graft.
Figure 3:
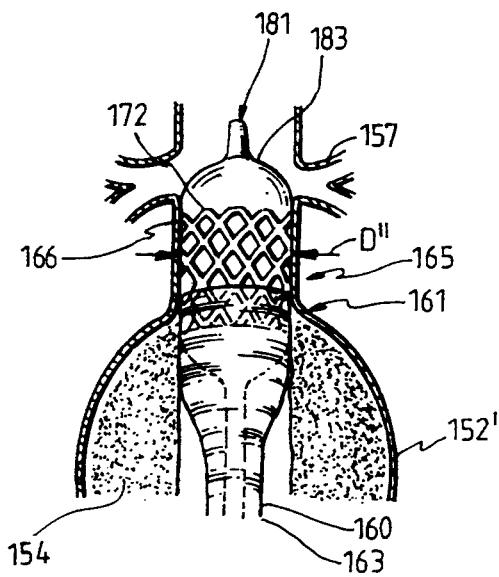
FIG. 3 is a partial cross-sectional view of the aorta of FIG. 2, illustrating the portion of the aortic graft being fully expanded.
Figure 4:
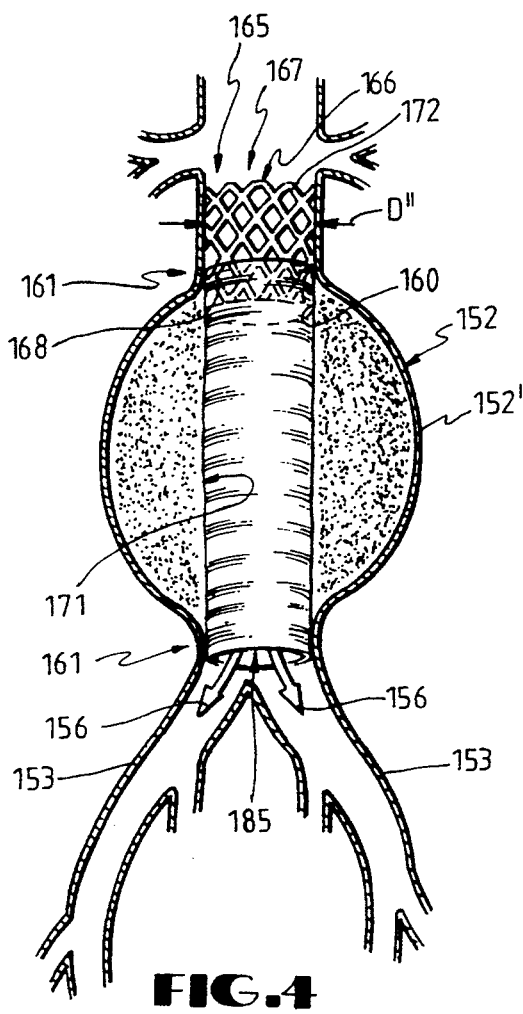
FIG. 4 is a partial cross-sectional view of an aorta with the aortic graft of the present invention having been used to repair an abdominal aortic aneurysm.

Preferably, securing means 165 includes a thin-walled member 166 having first and second ends 167, 168 and a smooth outer wall surface 169 disposed between the first and second ends 167. 168 of the thin-walled member 166. The thin-walled member 166 has a first diameter D' (FIG. 1), which permits intraluminal delivery of the thin-walled member 166 into the aorta 152. Upon the application from the interior of the thin-walled member 166 of a radially, outwardly extending force, as will be hereinafter described in greater detail, the thin-walled member 166 has a second, expanded and deformed diameter D" (FIGS. 3 and 4), whereby the thin-walled member 166 is expanded and deformed to secure the first end 167 of the thin-walled member 166 and the first end 161 of the tube 160 to the aorta 152. The second diameter D", as will be hereinafter described in greater detail, is variable and dependent upon the amount of force applied to the thin-walled member 166. The first end 161 of tube 160 is connected to the second end 168 of the thin-walled member 166, as by a plurality of sutures 170 (FIG. 2). Sutures 170 may be conventional sutures of polypropylene, DACRON ®, or any other suitable material. Preferably, the first end 161 of tube 160 overlaps and covers the second end 168 of thin-walled member 166, such overlap being approximately 50% of the length of thin-walled member 166. The first end 161 of tube 160, which overlaps the second end 168 of thin-walled member 166, is preferably constructed so that it is radially expandable, whereby the first end 161 of tube 160 may conform with the second, expanded and deformed diameter D" of the second end 168 of the thin-walled member 166 as seen in FIGS. 3 and 4. If tube 160 is woven, the weave of the material at its first end 161 is looser, so that the desired radial expansion can be obtained. The intermediate portion 171 of tube 160 disposed between first and second ends 161, 162 thereof, is preferably not substantially radially expandable.

Still with reference to FIGS. 1–4, thin-walled member 166 is preferably a thin-walled tubular member 172 whose wall surface 169 has a substantially uniform thickness with a plurality of slots 173 (FIGS. 1 and 5) formed therein, the slots 173 being disposed substantially parallel to the longitudinal axis of the tubular member 172. It has been found that one type of thin-walled member 166, or tubular member 172, which is particularly useful as securing means 165 are the expandable intraluminal grafts disclosed in U.S. Pat. No. 4,733,665, issued Mar. 29, 1988; U.S. Pat. No. 4,739,762, issued Apr. 26, 1988; and U.S. Pat. No. 4,776,337, issued Oct. 11, 1988, all the foregoing patents being in the name of Julio C. Palmaz, and assigned to Expandable Grafts Partnership. Each of these patents is incorporated herein by reference. Other thin-walled members 166, or tubular members 172 could be utilized as securing means 165, provided they have ability to be controllably expanded and deformed from the first diameter D', which permits intraluminal delivery of securing means 165, to the second expanded and deformed diameter D", in order to secure the thin-walled member 166, and connected tube 160 within aorta 152.

Still with reference to FIGS. 1–4, tube 160, preferably has a generally, circular cross-sectional configuration, and tube 160 may be made from a variety of materials, provided they have the requisite strength characteristics to be utilized as an aortic graft 150, as well as have the requisite compatibility with the human body in order to be used as a graft, or implant material, without being rejected by the patient's body. Examples of such materials are DACRON ® and other polyester materials, TEFLON ® (polytetrafluoroethylene), TEFLON ® coated DACRON ® material and porous polyurethane. The material can be knitted or woven, and can be warp or weft knitted. If the material is warp knitted, it may be provided with a velour, or towel like surface, which speeds up clotting of blood which contacts tube 160 in order to increase the attachment, or integration, of tube 160 to aorta 152, or to assist the integration of tube 160 to the thrombosis 154. Tube 160 can also be made of a bio-erodable, or degradable material, such as albumin or collagen or a collagen coated material. A tube 160 which is bio-erodable, would erode and dissolve, or degrade, over a period of time; however, it is believed that a layer of endothelium, or skin, will grow as the tube 160 erodes, the new layer of endothelium, or skin, providing a new, fluid impervious lining within aneurysm 151. As will be hereinafter described in greater detail, when aortic graft 150 is utilized in connection with an emergency insertion after a rupture of aneurysm 151, it would be preferable to make tube 160 of a fluid impervious material. Additionally, the tube 160 or securing means 165 could have a coating of a biologically inert material, such as TEFLON ® or porous polyurethane.

Still with reference to FIGS. 1–4 tube 160 may have a crimped configuration to form an undulating longitudinal cross-sectional configuration (FIG. 1), whereby kinking, or twisting, or folding over upon itself will be minimized when the tube 160 is secured within the aneurysm 151, as will be hereinafter described in greater detail, This undulating configuration can be obtained by heat stamping tube 160, or in any other suitable manner, whereby the tube 160 has a "memory" and if it is twisted or kinked, it will return to its original configuration and disposition, Alternatively, tube 160 can have a smooth outer surface.

With reference to FIGS. 1–4, and FIG. 5, an apparatus 180 for repairing an abdominal aortic aneurysm 151 generally comprises: tube 160; expandable and deformable thin-walled member 166, or tubular member 172 which preferably includes slots 173 and has a smooth outer wall surface 169, the expansion and deformation of the thin-walled member 166 being controllable, as will hereinafter be described in greater detail; and a catheter 181 having an expandable, inflatable portion 182, or balloon 183 associated therewith and a nosepiece 184. The thin-walled member 166, or tubular member 172, is releasably mounted to the inflatable portion 182 of catheter 181, in any suitable fashion, whereby upon inflation of the expandable, inflatable portion 182 of catheter 181, the thin-walled member 166 is forced radially outwardly into contact with the aorta 152 to remain secured thereto, whereby the tube 160, secured to the thin-walled member 166, provides a passageway 185 (FIG. 4) through the abdominal aortic aneurysm 151, so that blood can pass through the aneurysm 151 and be separated therefrom. As seen in FIG. 4, the existing aortic wall 152' and the thrombosis 154 therein provide additional support and reinforcement for tube 160 of aortic graft 150.

Figure 5:
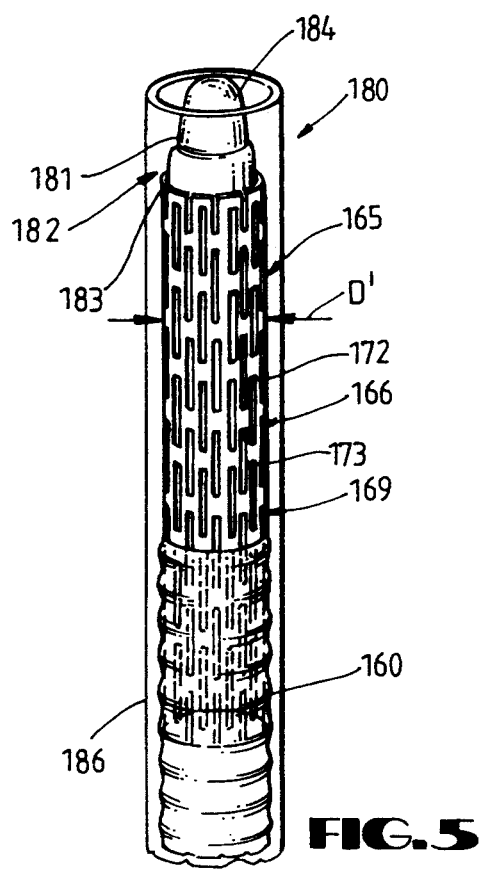
FIG. 5 is a perspective view of an apparatus for repairing an abdominal aortic aneurysm.

The apparatus 180 for repairing the abdominal aortic aneurysm 151 as illustrated in FIG. 5 is in its configuration it would have for intraluminal delivery, as also illustrated in FIG. 1. In the configuration shown in FIG. 5, the thin-walled member 166 has its first unexpanded, undeformed diameter D', and balloon 183 is shown partially inflated in FIG. 2, and completely inflated in FIG. 3. Expansion and deformation of thin-walled member 166 is controlled by the expansion of balloon 183 of catheter 181, in a conventional manner. When apparatus 180 is being intraluminally delivered, catheter 181, thin-walled member 166, and tube 160 are preferably enclosed by a conventional catheter sheath 186 which is removed, as shown in FIG. 1, as apparatus 180 is disposed in its desired location within aorta 152, as will hereinafter be described in greater detail. Deflation of balloon 183 permits the withdrawal of catheter 181 and release of the balloon 183 and catheter from aortic graft 150 after it has been disposed in the configuration shown in FIG. 4.

Figure 6:
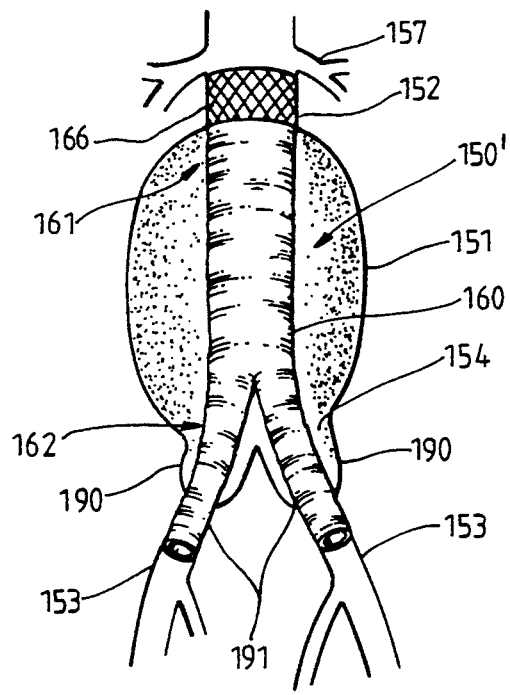
FIGS. 6–8 illustrates different embodiments of an aortic graft in accordance with the present invention, such grafts being disposed within an abdominal aortic aneurysm and/or iliac aneurysm.
Figure 8:
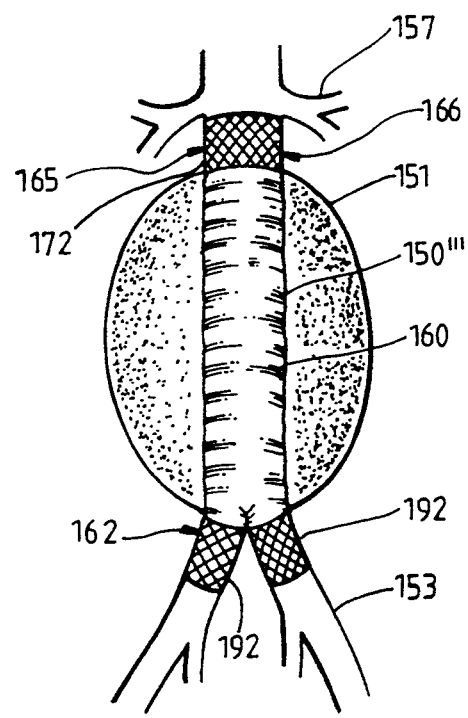
Figure 9:
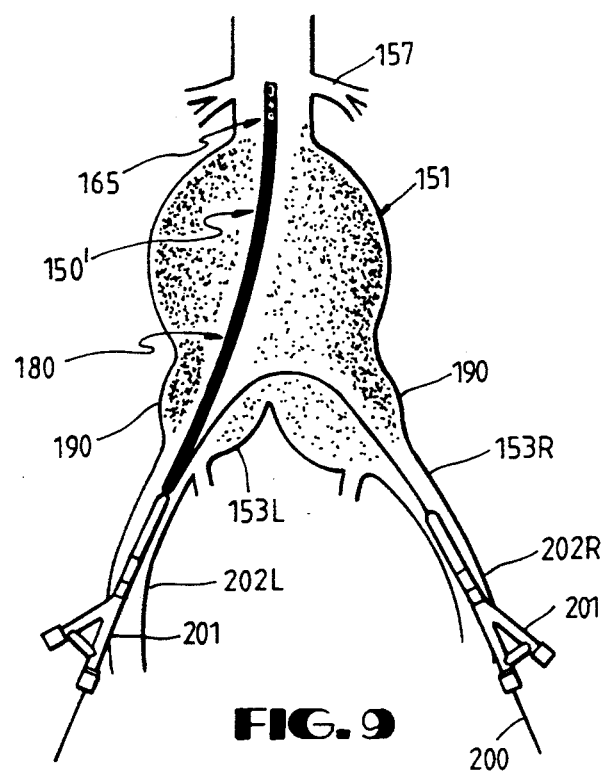
FIGS. 9–12 are partial cross-sectional views of an abdominal aortic aneurysm, illustrating one embodiment of the method of the present invention for repairing an abdominal aortic aneurysm and iliac aneurysm.

With reference to FIGS. 6 and 8, various embodiments of grafts 150 are illustrated within aorta 152 and aneurysm 151 after aneurysm 151 has been repaired through the use of aortic graft 150 and apparatus 180. In FIG. 6, aortic graft 150' includes tube 160 as previously described, and graft 150' is secured by use of thin-walled member 166 as previously described. Abdominal aortic aneurysm 151 also includes two iliac artery aneurysms 190, which also contain the same thrombosis 154 disposed within aneurysm 151. Aortic graft 150' of FIG. 6 has the second end 162 of tube 160 bifurcated, so that two tubular passageways 191 are formed which are each in fluid communication with the first end 161 of tube 160, and the fluid passageways 191 are mated with and disposed within the two iliac arteries 153.

Figure 7:
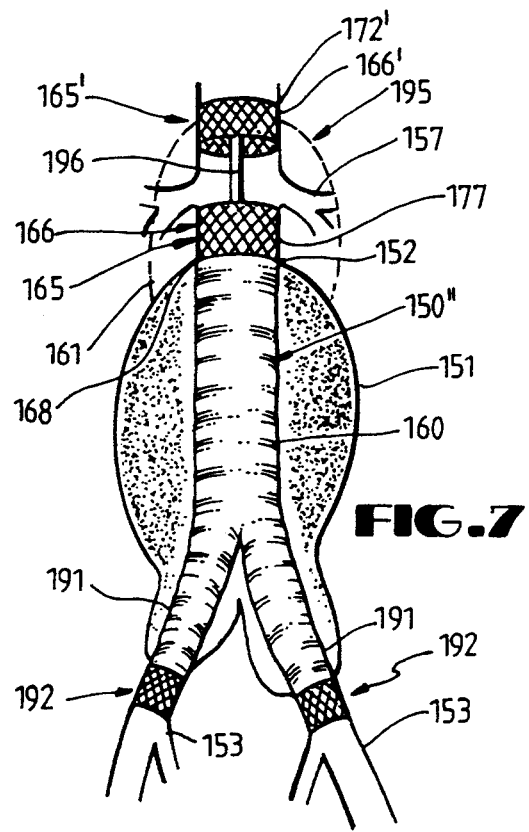

The aortic graft 150" of FIG. 7 is the same as graft 150' of FIG, 6, except that the two tubular passageways 191 include means for securing the two tubular passageways 191 to the two iliac arteries 153. Securing means 192 preferably are thin-walled members 166, or tubular members 172, of the same type of construction as those used for securing means 165. Securing means 192 may be expanded and deformed in the same manner as securing means 165 by controlled inflation of the expandable, inflatable portion 182 of catheter 181. In this regard, catheter 181 of apparatus 180 of FIG. 5 may include a second expandable, inflatable portion 182 (not shown) spaced longitudinally from the first expandable, inflatable portion 182, so that securing means 165 and 192 may be expanded and deformed simultaneously, Alternatively, apparatus 180 as shown in FIG. 5 could be utilized to first expand and deform securing means 165 disposed at the upper end 161 of tube 160, and the expandable, inflatable portion 182 could then be deflated and moved downwardly toward second securing means 192. The expandable, inflatable portion 182 would then be re-expanded and inflated to deform and expand securing means 192. Although the flow of pumped blood downwardly through aorta 152 and into iliac arteries 153 is believed to provide enough pressure to maintain passageway 191 in their desired positions, there is a slight negative vacuum pressure component associated with the pumping pressure, whereby the securing means 192 might be required. Securing means 192 also serves to insure no movement of passageways 191, caused by body movements.

In some instances, aneurysm 151 could extend above the renal arteries 157, as shown in dotted lines 195 in FIG. 7. In order to secure aortic graft 150" to repair such an aneurysm 151. 195, it is preferable to use a securing means 165' which includes first and second thin-walled members 166 and 166', or tubular members 172, 172', which are flexibly interconnected by at least one connector member 196, the first end 161 of tube 160 being secured, as previously described, to the second end 168 of thin-walled member 166 in the manner previously described. The flexible connector member 196 spans the part of the aorta 152 adjacent the renal arteries 157, so that fluid flow through renal arteries 157 is not obstructed. Preferably, two connector members 196 are utilized, the connector members being disposed 180° apart, whereby the surgeon can determine by x-ray or fluoroscopy that the two flexible connector members 196 are disposed in the position shown in FIG. 7, wherein the second connector member (not shown) is disposed directly behind the first connector member 196. If two images of connector members 196 appear on the x-ray or the fluoroscope, the surgeon will know that it is possible that one of the renal arteries 157 may be obstructed by one of the connector members 196. Securing means 165' is expanded and deformed in the same manner as previously described with respect to securing means 165.

With reference to FIG. 8, a graft 150''' is illustrated, graft 150''' being similar in design to the graft 150 illustrated in FIG. 4, with the exception that the second end 162 of tube 160 is provided with additional securing means 192 as previously described in connection with FIG. 7.

Figure 10:
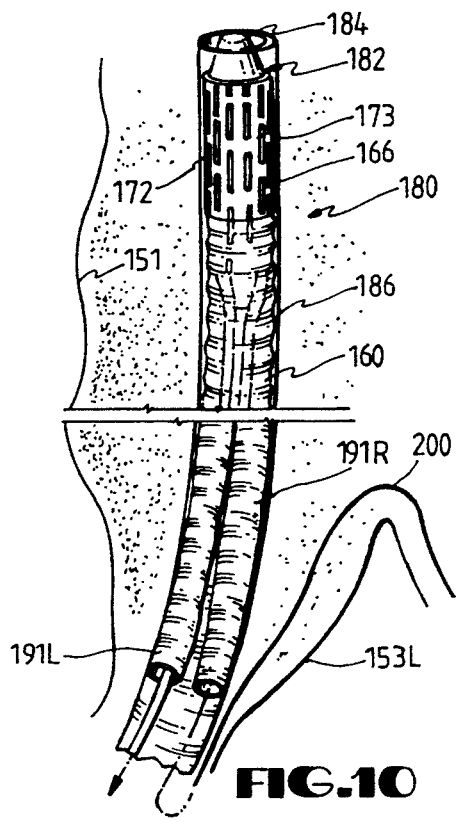
Figure 11:
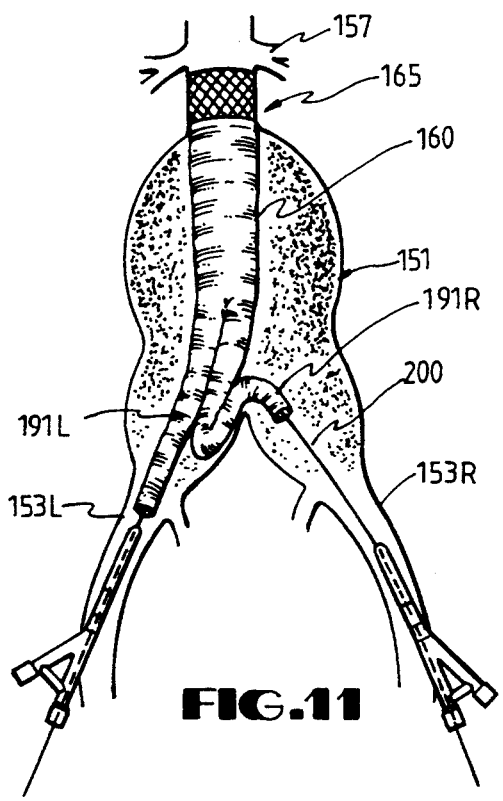
Figure 12:
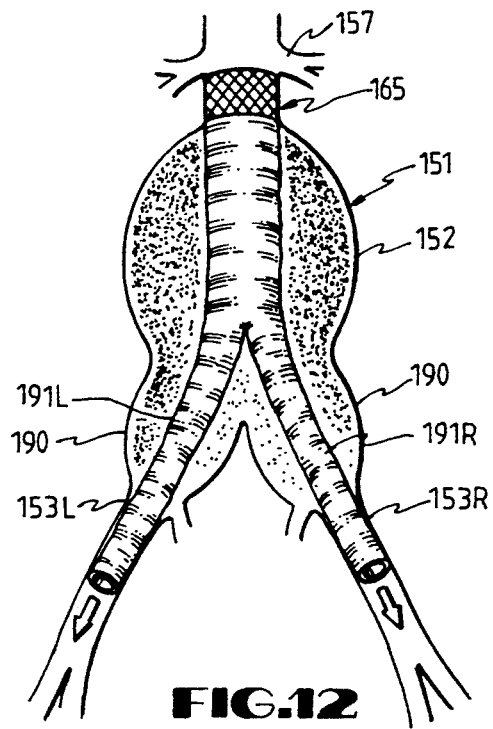

With reference to FIGS. 9–12, a method for repairing an abdominal aortic aneurysm 151 and iliac aneurysm 190 with an aortic graft 150' as illustrated in FIG. 6 will be described. After tube 160 has been connected to an expandable and deformable thin-walled member 166, or tubular member 172, as previously described in connection with FIGS. 1–5, a surgical wire 200 is introduced through a conventional catheter insertion device 201 through the right femoral artery 202R. In a conventional manner, the surgical wire 200 is passed from the right femoral artery 202R upwardly through the right iliac artery 153R through the aorta 152 and downwardly through the left iliac artery 153L and into the left femoral artery 202L and into another conventional catheter insertion device 201. Apparatus 180, including tube 160, catheter 181, and thin-walled member 166 are then intraluminally delivered into the aorta 152 and aneurysm 151, through the left femoral artery 202L, via a conventional catheter insertion device 201. Securing means 165 can be disposed in the aorta 152 in the position shown in FIGS. 9 and 1. Sheath 186 may then be removed in a conventional manner. With reference to FIGS. 10 and 11, after sheath 186 is removed, surgical wire 200 may then be sutured to the right passageway 191R of tube 160 as shown in FIG. 10. Securing means 165 may then be expanded and deformed in the manner previously described, as shown in FIG. 11. The wire 200 can then be withdrawn and pulled, so as to pull the right passageway 191R of tube 160 downwardly into the right iliac artery 153R until it assumes the position shown in FIG. 12. This same method could also be utilized to repair an aneurysm 151, including an iliac aneurysm 191 with the graft 150'' of FIG. 7.

Figure 13:
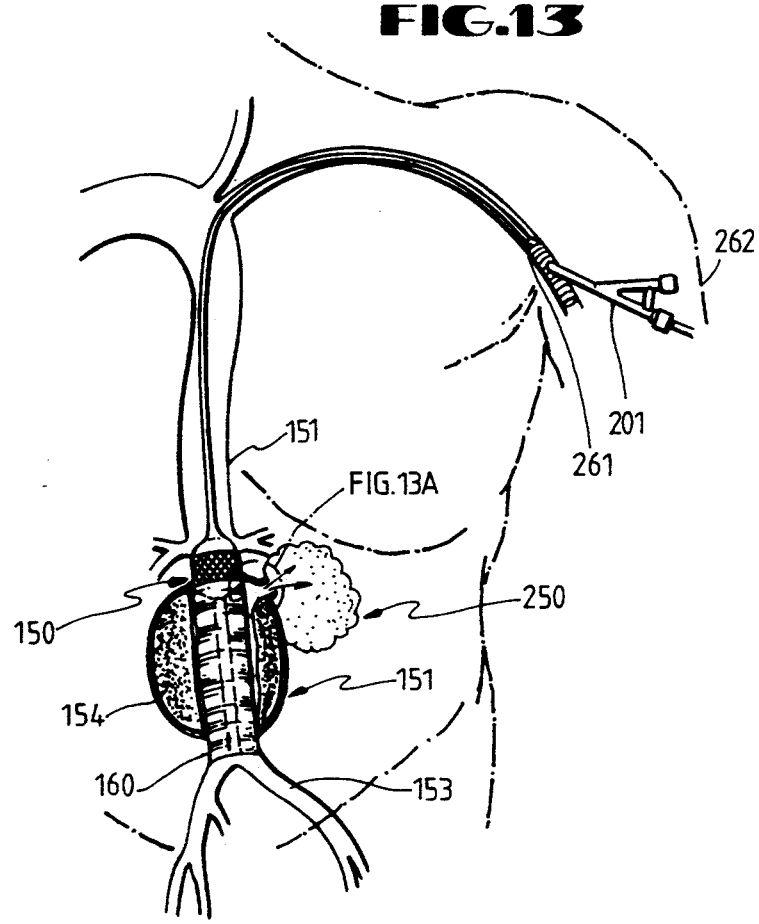
FIG. 13 is a partial cross-sectional view of a patient with a ruptured abdominal aortic aneurysm, which rupture is being repaired in accordance with the present invention.
Figure 13A:
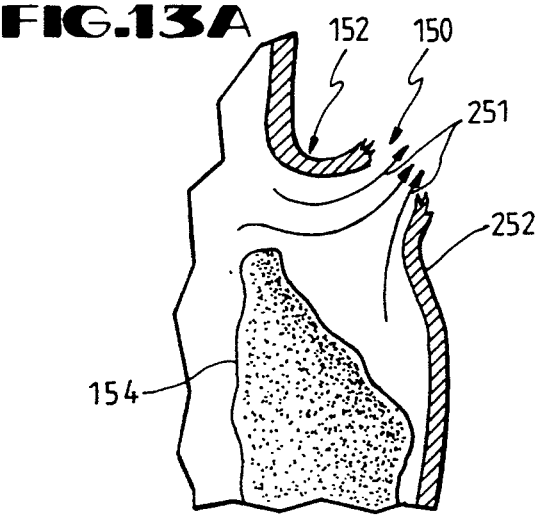
FIG. 13a is an enlarged partial cross-sectional view of a portion of FIG. 13.
Figure 14:
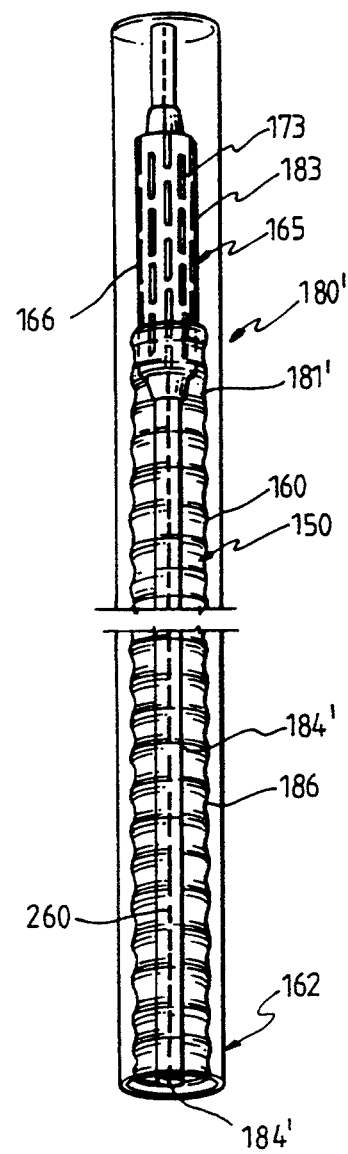
FIG. 14 is a partial cross-sectional view along the longitudinal axis of an apparatus for repairing an abdominal aortic aneurysm, after the aneurysm has ruptured.

With reference to FIGS. 13, 13a, and 14, a method and apparatus for repairing an abdominal aortic aneurysm 151 which has ruptured as shown at 250 in FIGS. 13 and 13a is illustrated. As seen in FIG. 13a, blood is illustrated by arrows 251 as flowing through the opening, or rupture, 250 in the wall 252 of aorta 152, and the thrombosis 154 is separated from wall 252. Apparatus 180', as shown in FIG. 14, is similar to apparatus 180 previously described in connection with FIG. 5. Apparatus 180' includes tube 160 of the type as previously described, a catheter 181' having an extended nosepiece 184', tube 160 being disposed about the extended nosepiece 184'. Securing means 165, as previously described, is mounted upon an expandable, inflatable portion 183 of catheter 181'. Apparatus 180' differs from that previously described, in that catheter 181' first passes through securing means 165 and then into tube 160, whereas in apparatus 180, catheter 181 first passes through tube 160 and then into securing means 165. Sheath 186 is also provided as previously described. Additionally, the second end 162 of tube 160 is restrained in the position shown in FIG. 14, as by a thread which passes through the lower end 162 of tube 160, the thread 260 passing through the extended catheter nosepiece 184'. As will hereinafter be described in greater detail, it is preferable that thread 260 be able to be easily pulled through tube 160. Accordingly, it is preferred that thread 260 have a smooth, slippery surface. Nylon monofilament is thus a preferred material for thread 260.

As seen in FIG. 13, apparatus 180' is intraluminally delivered to the aorta and the ruptured aneurysm 151 through an axillary artery 261 in the patient's arm 262 whereby apparatus 180' is intraluminally delivered via the axillary artery downwardly through the aorta 152 into the position illustrated in FIGS. 13 and 1. Securing means 165 is then expanded and deformed in the manner previously described, so that aortic graft 150 assumes the configuration illustrated in FIGS. 4 and 13. Thread 260 is then pulled and removed from tube 160 by pulling it out through nosepiece 184'. In the event of a rupture 250, it is believed it would be difficult to enter the aorta 152 from the femoral artery, where as it is believed it will be readily possibly to intraluminally deliver apparatus 180' through the axillary artery 261 via usage of a conventional catheter insertion device 201. Because of the rapid flow of blood, it is preferred that the tube 160 be made fluid impervious when used for repairing aneurysms which have ruptured. It should be readily recognized that the procedure illustrated in connection with FIGS. 13, 13a, and 14 can be much more expeditiously performed then the conventional, prior art method for repairing a ruptured aneurysm 151.

It is to be understood that the invention is not limited to the exact details of construction, operation, exact materials or embodiments shown and described, as obvious modifications and equivalents will be apparent to one skilled in the art. For example, the expandable, inflatable portion of the catheter could be a plurality of hydraulically actuated rigid members disposed on a catheter or a plurality of balloons could be utilized to expand the securing means. Additionally, the wall surface of the thin-walled member could be formed by a plurality of wires having a smooth exterior surface. Accordingly, the invention is therefore to be limited only by the scope of the appended claims.

We claim:

1. An aortic graft for intraluminal delivery to repair an abdominal aortic aneurysm in an aorta having two iliac arteries associated therewith, comprising:

a tube having first and second ends and a wall surface disposed between the two ends, at least a portion of the tube adapted to be disposed within the abdominal aortic aneurysm; and means for securing the first end of the tube to the aorta, the securing means including a thin-walled tubular member having a longitudinal axis, an interior, first and second ends and a smooth outer tubular member wall surface disposed between the first and second ends, the tubular member wall surface having a substantially uniform thickness and a plurality of slots formed therein, the slots being disposed substantially parallel to the longitudinal axis of the tubular member, the first end of the tube being secured to the second end of the tubular member; the tubular member having a first diameter which permits intraluminal delivery of the tubular member into the aorta and the tubular member having a second, expanded and deformed diameter, upon an application from the interior of the tubular member of a radially, outwardly extending force, which second diameter is variable and dependent upon the force applied to the tubular member, whereby the tubular member may be expanded and deformed to secure the first end of the tubular member to the aorta.

2. The aortic graft of claim 1, wherein the slots are uniformly and circumferentially spaced from adjacent slots and the slots are uniformly spaced from adjacent slots along the longitudinal axis of the tubular member, whereby at least one elongate member is formed between adjacent slots.

3. The aortic graft of claim 2, wherein each slot has first and second ends, and the first and seconds ends of each slot are disposed intermediate the first and second ends of adjacent slots along the longitudinal axis of the tubular member.

4. The aortic graft of claim 1, wherein the tubular member does not exert any outward, radial force while the tubular member has the first or second expanded diameter.

5. The aortic graft of claim 1, wherein the slots have a substantially rectangular configuration when the tubular member has the first diameter; and the slots have a substantially hexagonal configuration when the tubular member has the second, expanded diameter.

6. The aortic graft of claim 1, wherein the tubular member has a biologically inert coating on the wall surface.

7. The aortic graft of claim 1, wherein the second end of the tube is bifurcated and two tubular passageways are formed which are in fluid communication with the first end of the tube and the two passageways are adapted to be mated with and disposed within two illiac arteries.

8. The aortic graft of claim 7, wherein the two tubular passageways include means for securing the two tubular passageways to the two illiac arteries.

9. The aortic graft of claim 8, wherein the securing means includes a thin-walled tubular member having first and second ends and a smooth outer wall surface disposed between the first and second ends, the wall surface having a substantially uniform thickness and a plurality of slots formed therein, the slots being disposed substantially parallel to the longitudinal axis of the tubular member, the fluid passageways being secured to the first end of the tubular member; the tubular member having a first diameter which permits intraluminal delivery of the tubular member into the aorta and the tubular member having a second, expanded and deformed diameter, upon the application from the interior of the tubular member of a radially, outwardly extending force, which second diameter is variable and dependent upon the amount of force applied to the tubular member, whereby the tubular member may be expanded and deformed to secure the second end of the tubular member and the tubular passageways to the two illiac arteries.

10. The aortic graft of claim 1, wherein the first end of the tube is secured to the second end of the tubular member by a plurality of sutures.

11. The aortic graft of claim 1, wherein the first end of the tube which is secured to the second end of the tubular member is radially expandable, whereby the first end of the tube may conform with the second expanded and deformed diameter of the second end of the tubular member.

12. The aortic graft of claim 1, wherein the tube has an intermediate portion which is not substantially radially expandable.

13. The aortic graft of claim 1, wherein the tube is crimped to forte an undulating longitudinal cross-sectional configuration, whereby kinking or twisting of the tube is minimized.

14. The aortic graft of claim 1, wherein the securing means includes first and second tubular members flexibly interconnected by at least one connector member, the first end of the tube being secured to one of the tubular members.

15. The aortic graft of claim 1, wherein the tube is bio-erodable.

16. The aortic graft of claim 1, wherein the tube is impervious to the flow of fluid through the wall surface of the tube.

17. The aortic graft of claim 1, wherein the first end of the tube overlaps and covers the second end of the tubular member.

18. The aortic graft of claim 17, wherein the tubular member has a length and the overlap is approximately 50% of the length of the tubular member.

* * * * *

UNITED STATES PATENT AND TRADEMARK OFFICE
CERTIFICATE OF CORRECTION

PATENT NO. : 5,360,443

DATED : November 1, 1994

INVENTOR(S) : Hector D. Barone, Juan C. Parodi and Julio C. Palmaz

It is certified that error appears in the above-identified patent and that said Letters Patent is hereby corrected as shown below:

Column 12, claim 13, line 2, "forte" should read --form--.

In claim 13, line 2, "forte" should read --form--.

Signed and Sealed this

Twenty-eight Day of March, 1995

Attest:

BRUCE LEHMAN

Attesting Officer     Commissioner of Patents and Trademarks